(12) United States Patent
Wiedmann

(10) Patent No.: US 9,417,194 B2
(45) Date of Patent: Aug. 16, 2016

(54) ASSESSMENT OF FOCAL SPOT CHARACTERISTICS

(71) Applicant: General Electric Company, Schenectady, NY (US)

(72) Inventor: Uwe Wiedmann, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 214 days.

(21) Appl. No.: 13/969,279

(22) Filed: Aug. 16, 2013

(65) Prior Publication Data

US 2015/0049857 A1 Feb. 19, 2015

(51) Int. Cl.
*A61B 6/03* (2006.01)
*G01N 23/04* (2006.01)
*A61B 6/00* (2006.01)

(52) U.S. Cl.
CPC .............. *G01N 23/046* (2013.01); *A61B 6/032* (2013.01); *A61B 6/4021* (2013.01); *A61B 6/58* (2013.01); *A61B 6/582* (2013.01); *A61B 6/4441* (2013.01); *G01N 2223/303* (2013.01); *G01N 2223/316* (2013.01); *G01N 2223/32* (2013.01)

(58) Field of Classification Search
CPC .............. G21K 1/02; A61B 6/02; A61B 6/03; A61B 6/032; A61B 6/583; A61B 6/4021; A61B 6/4441; A61B 6/582; A61B 6/58; G01N 23/046; G01N 2223/32; G01N 2223/303; G01N 2223/316303; G01N 2223/316
See application file for complete search history.

(56) References Cited

U.S. PATENT DOCUMENTS

| | | | |
|---|---|---|---|
| 4,675,892 A | 6/1987 | Plessis et al. | |
| 4,803,711 A * | 2/1989 | Tsujii et al. | 378/4 |
| 5,550,886 A | 8/1996 | Dobbs et al. | |
| 6,094,469 A * | 7/2000 | Dobbs et al. | 378/19 |
| 6,327,331 B1 | 12/2001 | Toth et al. | |
| 6,438,207 B1 | 8/2002 | Chidester et al. | |
| 6,652,143 B2 | 11/2003 | Popescu | |
| 7,249,886 B1 * | 7/2007 | Chao et al. | 378/207 |
| 7,257,194 B2 | 8/2007 | Smith | |
| 7,286,639 B2 | 10/2007 | Shen et al. | |
| 7,409,043 B2 | 8/2008 | Dunham et al. | |
| 7,486,776 B2 | 2/2009 | Andrews et al. | |
| 7,507,026 B2 | 3/2009 | Andrews et al. | |
| 7,654,740 B2 | 2/2010 | Behling et al. | |
| 7,794,144 B2 | 9/2010 | Windt | |
| 2006/0011852 A1 * | 1/2006 | El-Hanany et al. | 250/370.09 |
| 2008/0317200 A1 * | 12/2008 | Lecomte et al. | 378/19 |
| 2009/0003519 A1 * | 1/2009 | Defreitas et al. | 378/37 |
| 2010/0020938 A1 | 1/2010 | Koch et al. | |
| 2010/0158318 A1 | 6/2010 | Snoeren | |

OTHER PUBLICATIONS

Dabrowski et al., X-ray imaging inside the focal spot of polycapillary optics using the coded aperture concept, Feb. 2013, Optics Express, vol. 21, No. 3, p. 2921-2923, 2927.*

(Continued)

*Primary Examiner* — Glen Kao
(74) *Attorney, Agent, or Firm* — Melissa K. Dobson

(57) ABSTRACT

Use of a reference detector to characterize an X-ray emission focal spot is disclosed. In certain embodiments, the reference detector may contain one or more openings or apertures that may be used to acquire localized X-ray intensity information used to derive the focal spot characteristics. In certain embodiments, the reference detector is on the source-side of the imaged volume.

20 Claims, 15 Drawing Sheets

(56) References Cited

OTHER PUBLICATIONS

Russo et al., "Method for Measuring the Focal Spot Size of an X-Ray Tube Using a Coded Aperture Mask and a Digital Detector", Medical Physics, vol. 38, Issue 4, pp. 2099-2115, Mar. 23, 2011.

Rong et al., "Measurement of Focal Spot Size with Slit Camera Using Computed Radiography and Flat-Panel Based Digital Detectors", Medical Physics, vol. 30, Issue 7, pp. 1768-1775, Jun. 25, 2003.
Watson, "Real-Time Spot Size Measurement for Pulsed High-Energy Radiographic Machines", IEEE, vol. 3, pp. 2447-2449, May 1993, Washington DC.

* cited by examiner

ASSESSMENT OF FOCAL SPOT CHARACTERISTICS

BACKGROUND

The subject matter disclosed herein relates to focal spot evaluation in X-ray devices.

In modern medicine, medical professionals routinely conduct patient imaging examinations to assess the internal tissue of a patient in a non-invasive manner. Furthermore, for industrial applications related to security or quality control, screeners may desire to non-invasively assess the contents of a container (e.g., a package or a piece of luggage) or the internal structure of a manufactured part. Accordingly, for medical, security, and industrial applications, X-ray imaging techniques may be useful for noninvasively characterizing the internal composition of a subject of interest.

X-ray imaging techniques typically involves the generation of X-rays from a source, such as an X-ray tube. Such X-ray emitters typically utilize an emitter that emits electrons that are electro-statically or magnetically focused on a target that emits X-rays in response to the electron stream. In such contexts, the impact region of the electrons on the target is known as the focal spot. The characteristics (e.g., position, size, and so forth) of the focal spot may difficult to maintain within the desired tolerances or may otherwise vary during operation. It may be useful to know the characteristics of the focal spot in a real-time manner as these characteristics may impact the image quality of images generated using the emitted X-rays and/or may be useful to know in the reconstruction of such images. Similarly, such characteristics, when measured in real-time, may be used as part of a real-time feedback loop to maintain the focal spot within the desired tolerances.

BRIEF DESCRIPTION

In one embodiment, a CT system is provided. The CT system comprises an X-ray source comprising a target material. The X-ray source is disposed on a first side of an imaging volume. The CT system further comprises an imaging detector configured to generate a first set of electrical signals in response to a first portion of the X-rays emitted by the X-ray source. The imaging detector is disposed on a second side of the imaging volume opposite the first side. The CT system also comprises a reference detector positioned on the first side of the imaging volume. The reference detector is configured to generate a second set of electrical signals in response to a second portion of the X-rays emitted by the X-ray source. The CT system further comprises a data acquisition system configured to receive the first set of electrical signals from the imaging detector and the second set of imaging signals from the reference detector and a processing component configured to process the second set of imaging signals to generate measures of one or more characteristics of a focal spot on the target when X-rays are emitted by the X-ray source.

In a further embodiment, a reference detector is provided. The reference detector comprises an X-ray lens assembly. The X-ray lens assembly comprises at least one central aperture is configured to transmit X-rays emitted by the X-ray source and two or more slits or holes on opposing sides of the central aperture. Each slit or hole is configured to transmit X-ray for a localized sub-region of the focal spot.

In an additional embodiment, a method for characterizing an X-ray generation focal spot is provided. In accordance with the method, during operation of an X-ray source, localized intensity measurements are acquired from a reference detector. The localized intensity measurements are associated with a focal spot of the X-ray source. One or more characteristics of the focal spot are determined. The one or more characteristics of the focal spot are provided to a processing component or controller to adjust operation or collimation of the X-ray source.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present disclosure relates to the use of a reference detector that generates localized intensity information that may be used to characterize an X-ray emission focal spot, such as based on the shape, size, or location of the focal spot. In certain embodiments, the reference detector discussed herein contains one or more openings or apertures (such as slits or holes) that may be used to acquire localized intensity information that may in turn be processed to derive the focal spot characteristics in question. As discussed herein, the reference detector may be separate from the primary, or imaging, detector used to acquire projection data used to reconstruct diagnostic images. Similarly, in certain such embodiments the reference detector is on the source-side of the imaged volume, as opposed to being on the detector-side of the volume. The derived focal spot characteristics can be used in real-time to control an X-ray imaging operation of a patient, such as by adjusting collimator blades used to shape and direct the X-ray emissions into the imaged volume. In such an implementation, real-time adjustment of the collimator blades in response to the derived focal spot characteristics can reduce or eliminate image artifacts that might otherwise result from the collimator blades not being properly directed to the emission focal spot (i.e., being misaligned). In addition, the focal spot characteristics may be used to control or adjust operation of the X-ray source, such as electrical parameters that influence focal spot size and/or focal spot position, and/or to adjust a reconstruction operation performed by the imaging system.

Measurement of focal spot characteristics may be particularly useful in certain contexts. For example, certain X-ray imaging systems may use a classical or more advanced emitter structure (as discussed in U.S. Patent Application No. 2011/0142193 A1, which is herein incorporated by reference in its entirety for all purposes) to generate the electron beam used in X-ray generation. Magnetic focusing or magnetic deflection may be utilized to steer or guide the electron beam. However, in such contexts focal spot size on the target may be highly sensitive to changes or variation in the electron beam current or the magnetic focusing and/or deflection currents, which can lead to image artifacts. For example, in extreme cases as little as a 1% change in magnet current can result in a 50% change in focal spot size. As discussed herein, real-time measurement of focal spot characteristics (such as size, location, and/or shape) may help to reduce the effects of such variation or may allow for control schemes to reduce, mitigate, or eliminate such focal spot variation.

Figure 1:
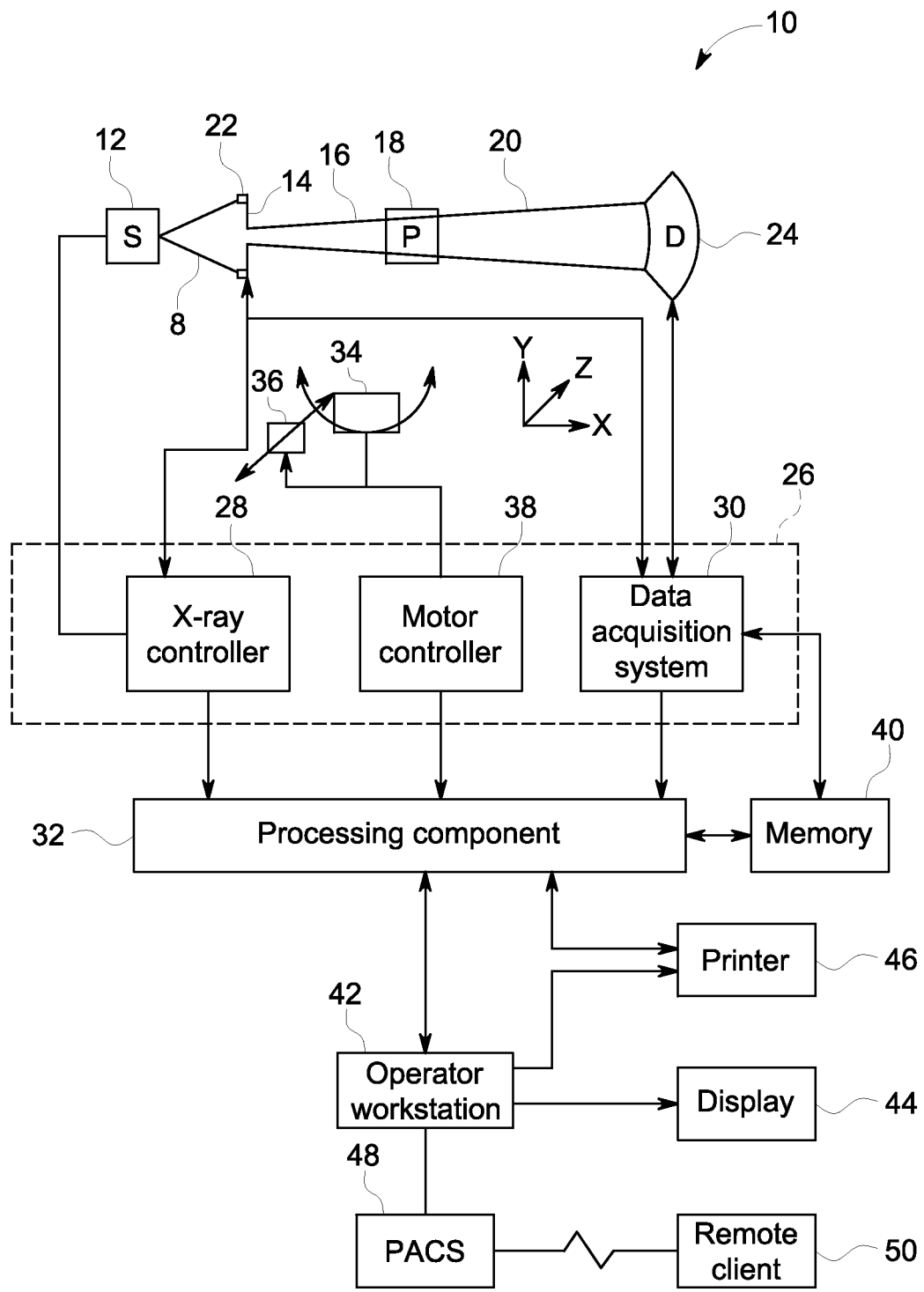
FIG. 1 is a diagrammatical view of a CT imaging system for use in producing images, in accordance with aspects of the present disclosure.

With this in mind, an example of an imaging system 10, such as a computed tomography (CT) system, suitable for use with the present focal spot assessment approaches is depicted in FIG. 1. Though a CT system is discussed with respect to FIG. 1, it should be appreciated that the system 10 and discussion related to CT imaging is provided merely to facilitate explanation by providing one example of a particular imaging context. However, the present approach is not limited to CT implementations and, indeed may be used in various other suitable imaging contexts where radiation is generated by using a focus beam (such as an electron beam). To facilitate explanation and to provide useful context and examples, the present discussion generally describes X-ray generation approaches where an electron beam is focused on some form of target material. However, it should be appreciated that the present approach is not limited to these contexts and may be used with other X-ray generation techniques, including techniques where no explicit target material is employed. For example, the present approach may also be useful in X-ray generation approaches where a laser beam and electron beam are collided in a cavity to generate X-rays.

Turning back to FIG. 1, in the depicted example, the imaging system 10 is designed to acquire X-ray attenuation data at a variety of view angles around a patient (or other subject or object of interest). In the embodiment illustrated in FIG. 1, imaging system 10 includes a source of X-ray radiation 12 positioned adjacent to a collimator 14. The X-ray source 12 may be an X-ray tube or other source of X-ray radiation.

In the depicted example, the generated X-rays 8 may be emitted over an angular range wider than needed for imaging purposes. A collimator 14 may be provided that shapes the emitted X-rays 8 into a shaped beam 16 of X-rays that is allowed to pass through the imaging volume in which a patient 18 is positioned. For example, in practice, the collimator 14 may comprise a set of adjustable blades or apertures constructed of a highly attenuating material. In operation, some X-rays are allowed to pass through the collimator 14, while others are blocked by the collimator 14. In the depicted example, the collimated X-rays 16 are in a fan-shaped or a cone-shaped beam that passes through the imaged volume. A portion of the X-ray radiation 20 passes through or around the patient 18 (or other subject of interest) and impacts an imaging detector array, represented generally at reference numeral 24. Detector elements of the array produce electrical signals that represent the intensity of the incident X-rays 20. These signals are acquired and processed to reconstruct images of the features within the patient 18.

In addition, FIG. 1 depicts a source-side reference detector (SSRD) 22 provided on the source-side of the imaged volume (as opposed to the detector-side). In the depicted example, the SSRD 22 is positioned on or in conjunction with the collimator 14 so as to be impacted by emitted radiation 8 that would otherwise be blocked by the collimator 14 from passing into the imaged volume. That is, in the depicted example the SSRD 22 detects emitted radiation 8 that would not be otherwise be used in image generation but which would otherwise be blocked by the collimator 14 (i.e., would not be part of the shaped beam 16). In the depicted example, the SSRD 22 and detector 24 provide separate signals to the data acquisition system 30. The SSRD 22 and its use are discussed in greater detail below.

In FIG. 1, the source 12 is controlled by a system controller 26, which furnishes both power, and control signals for examination sequences. In the depicted embodiment, the system controller 26 controls the source 12 via an X-ray controller 28 which may be a component of the system controller 26. In such an embodiment, the X-ray controller 28 may be configured to provide power and timing signals to the X-ray source 12.

Moreover, the detector 24 is coupled to the system controller 26, which controls acquisition of the signals generated in the detector 24. In the depicted embodiment, the system controller 26 acquires the signals generated by the detector 24 and by the SSRD 22 using a data acquisition system 30. The data acquisition system 30 receives data collected by readout electronics of the detector 24 and SSRD 22. The data acquisition system 30 may receive sampled analog signals from the detector 24 and SSRD 22 and may convert the data to digital signals for subsequent processing by a processor 32 discussed below. Alternatively, in other embodiments the analog-to-digital conversion may be performed by circuitry provided on the detector 24 or SSRD 22 itself. The system controller 26 may also execute various signal processing and filtration functions with regard to the acquired image signals, such as for initial adjustment of dynamic ranges, interleaving of digital image data, and so forth.

In the embodiment illustrated in FIG. 1, system controller 26 is coupled to a rotational subsystem 34. A linear positioning subsystem 36 may also be present in certain contexts, such as where the system 10 is a CT system. The rotational subsystem 34 enables the image acquisition components to be rotated one or multiple turns around the patient 18, such as rotated primarily in an x,y-plane about the patient (where the z-axis refers to the long axis of the patient). It should be noted that the rotational subsystem 34 might include a gantry or C-arm upon which the respective X-ray emission and detection components are disposed. Thus, in such an embodiment, the system controller 26 may be utilized to operate the gantry or C-arm.

The linear positioning subsystem 36, when present, may enable the patient 18, or more specifically a table supporting the patient, to be displaced, such as in the z-direction relative to rotation of the gantry or C-arm. Thus, the table may be linearly moved (in a continuous or step-wise fashion) to generate images of particular areas of the patient 18. In the depicted embodiment, the system controller 26 controls the movement of the rotational subsystem 34 and/or the linear positioning subsystem 36 via a motor controller 38. While the preceding discussion generalizes aspects of the various rotational and linear positioning systems that may be present, other positioning systems may be present and/or the linear or rotational positioning systems may include respective subsystems.

In general, system controller 26 commands operation of the imaging system 10 (such as via the operation of the source 12, detector 24, SSRD 22, and positioning systems described above) to execute examination protocols and to process acquired data. For example, the system controller 26, via the systems and controllers noted above, may rotate a gantry or C-arm supporting the source 12 and detector 24 about a subject of interest so that X-ray attenuation data may be obtained at a variety of views relative to the subject. In the present context, system controller 26 may also include signal processing circuitry, associated memory circuitry for storing programs and routines executed by the computer (such as routines for executing artifact reduction techniques described herein), as well as configuration parameters, image data, and so forth.

In the depicted embodiment, the image signals from the detector 24 and the reference signals from the SSRD 22 are acquired by the system controller 26 and provided to a processing component 32 for reconstruction of images. In certain embodiments, the system controller 26 may itself utilize the SSRD output (or measures generated from the SSRD output) to control operation of the X-ray source 12 and/or to control operation of the collimator 14, such as to allow real-time focal spot size control. The processing component 32 may, in certain embodiments, be one or more conventional microprocessors, such as general purpose microprocessors, or may take the form of application specific integrated circuits (ASICs). The data collected by the data acquisition system 30 may be transmitted to the processing component 32 directly or after storage in a memory 40. Any type of memory suitable for storing data might be utilized by such an exemplary system 10. For example, the memory 40 may include one or more optical, magnetic, and/or solid state memory storage structures. Moreover, the memory 40 may be located at the acquisition system site and/or may include remote storage devices for storing data, processing parameters, and/or routines for artifact reduction, as described below.

The processing component 32 may be configured to receive commands and scanning parameters from an operator via an operator workstation 42, typically equipped with a keyboard and/or other input devices. An operator may control the system 10 via the operator workstation 42. Thus, the operator may observe the reconstructed images and/or otherwise operate the system 10 using the operator workstation 42. For example, a display 44 coupled to the operator workstation 42 may be utilized to observe the reconstructed images and to control imaging. Additionally, the images may also be printed by a printer 46 which may be coupled to the operator workstation 42.

Further, the processing component 32 and operator workstation 42 may be coupled to other output devices, which may include standard or special purpose computer monitors and associated processing circuitry. One or more operator workstations 42 may be further linked in the system for outputting system parameters, requesting examinations, viewing reconstructed images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 42 may also be coupled to a picture archiving and communications system (PACS) 48. PACS 48 may in turn be coupled to a remote client 50, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 32, memory 40, and operator workstation 42 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 26 may be provided as part of such a computer or workstation or as part of a separate system dedicated to image acquisition.

Figure 2:
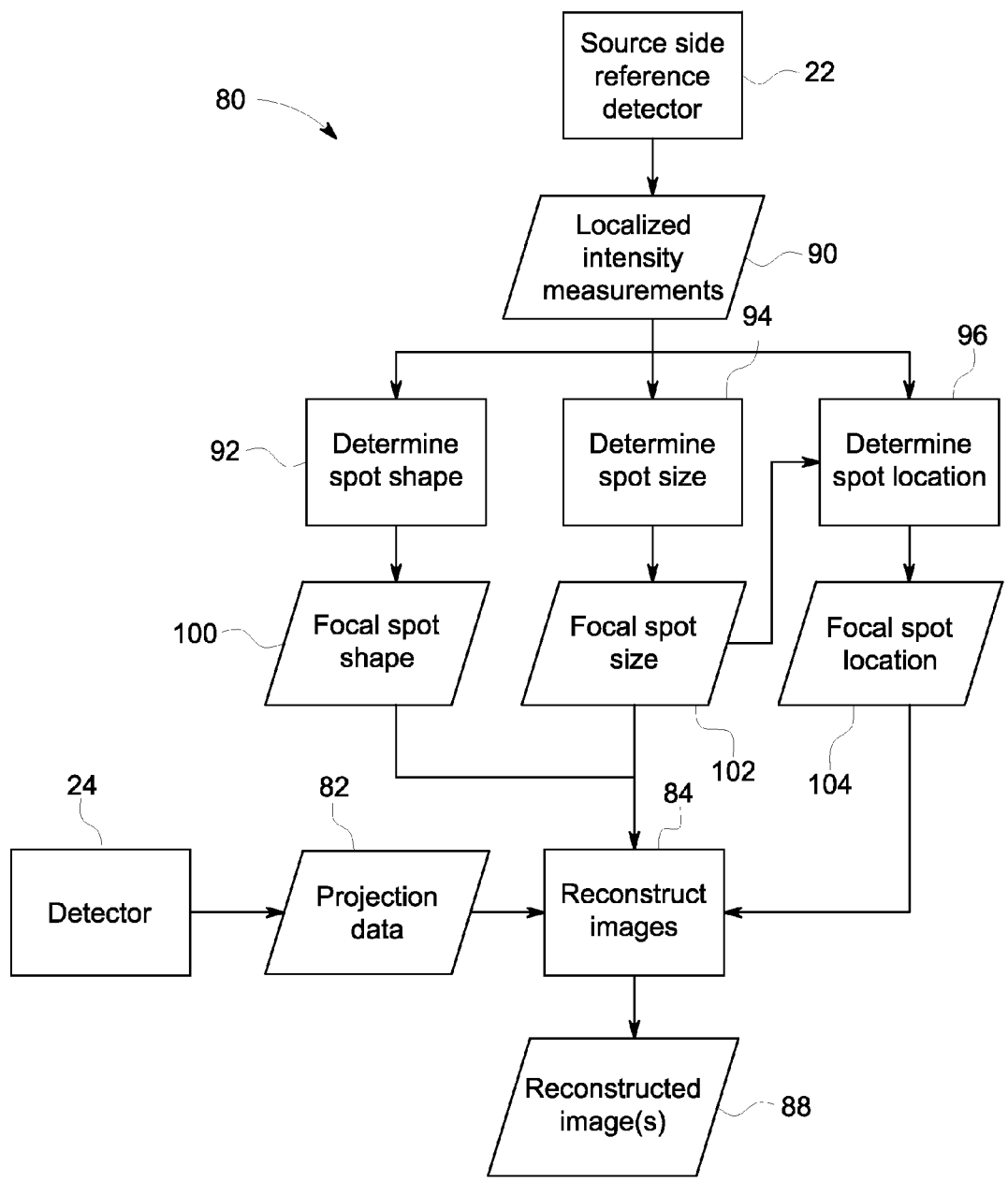
FIG. 2 depicts a flowchart depicting control logic for characterizing a focal spot, in accordance with aspects of the present disclosure.

With the foregoing discussion of a suitable implementation of an imaging system 10 in mind, FIG. 2 depicts a flowchart 80 describing an algorithm for image reconstruction using data derived from one or more source-side reference detectors (SSRD) 22 as well as data derived from the imaging detector 24. In this example, the imaging detector 24 acquires projection data 82 at a number of views about the imaged volume. The projection data 82 is reconstructed (block 84) to generate one or more reconstructed images 88. In the depicted example, the reconstruction step 84 may leverage a variety of data acquired via the SSRD 22 to improve the reconstruction process.

For example, in one implementation, the SSRD 22 can acquire a set of localized measurements 90 at some or all of the views for which projection data is also acquired. These localized measurements 90 may vary depending on configuration of the SSRD 22 and will be discussed in greater detail below. However, for the purpose of this example, the localized intensity measurements may be used to determine (blocks 92, 94, 96) one or more characteristics of the focal spot, such as focal spot shape 100, focal spot size 102, and focal spot location 104. To some extent, determination of one focal spot characteristic may be useful in determining another focal spot characteristic. For example, in the depicted implementation, focal spot size 102 may itself be an input to the focal spot location determination (block 96). One or both of the focal spot size 102 and the focal spot location 104 may be provided as inputs to the reconstruction step 84. Likewise, focal spot shape, if determined, may be provided as an input to the reconstruction step 84. While the present example demonstrates the use of focal spot characteristics to improve an image reconstruction process, as noted herein the focal spot characteristics may also be used, such as by a controller of the system controller 26, to adjust or control operation of the X-ray source 12 and/or to adjust the collimators 14. Indeed, such adjustments to the X-ray source operation or to collimator placement may occur essentially in real-time during an imaging operation to improve the quality of the projection data acquired.

Figure 3:
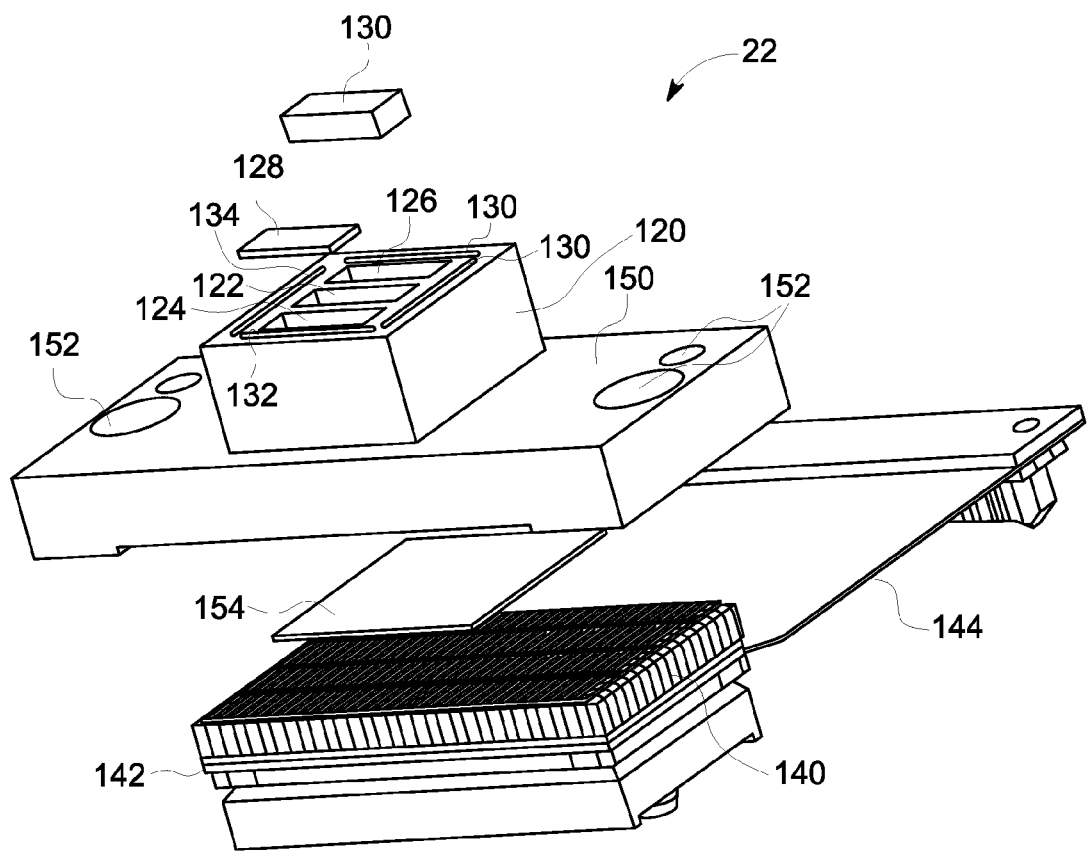
FIG. 3 depicts an exploded view of a source-side reference detector (SSRD), in accordance with aspects of the present disclosure.
Figure 4:
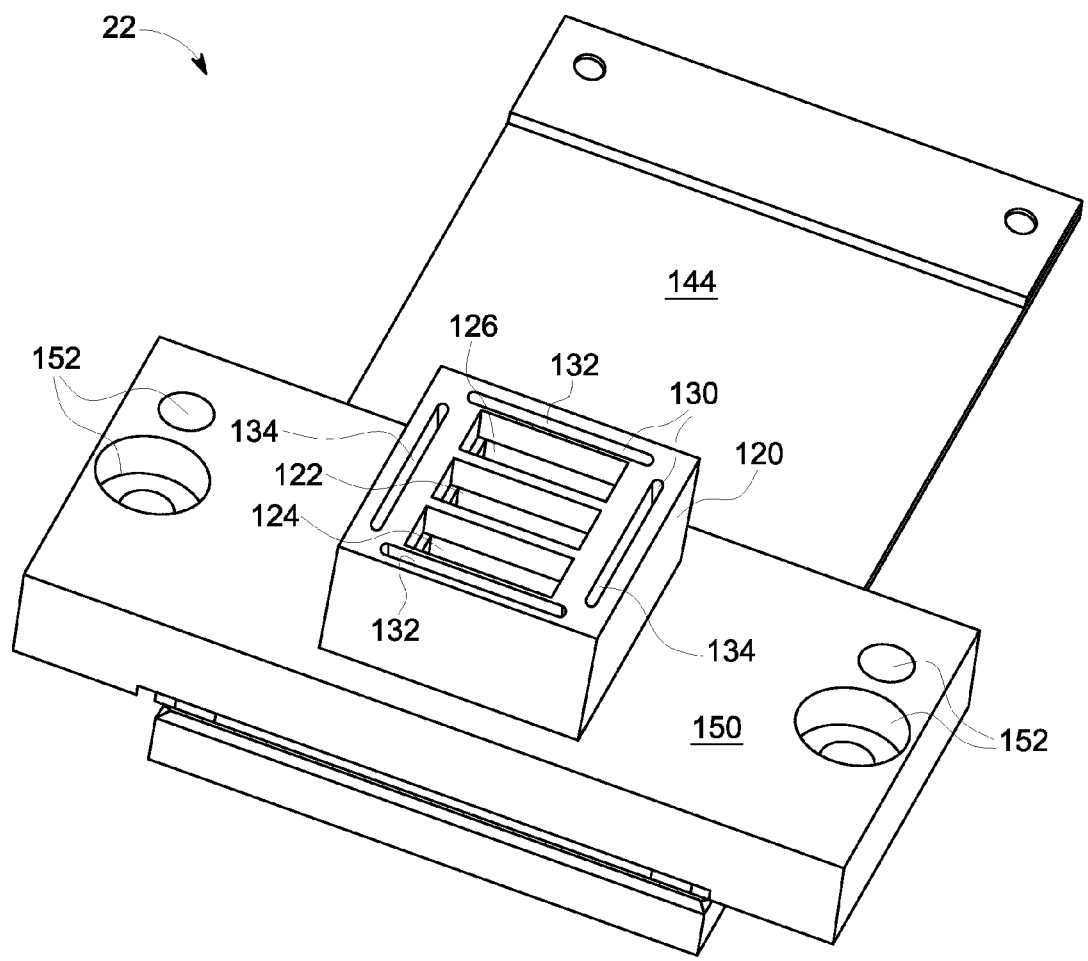
FIG. 4 depicts a perspective view of a SSRD, in accordance with aspects of the present disclosure.
Figure 5:
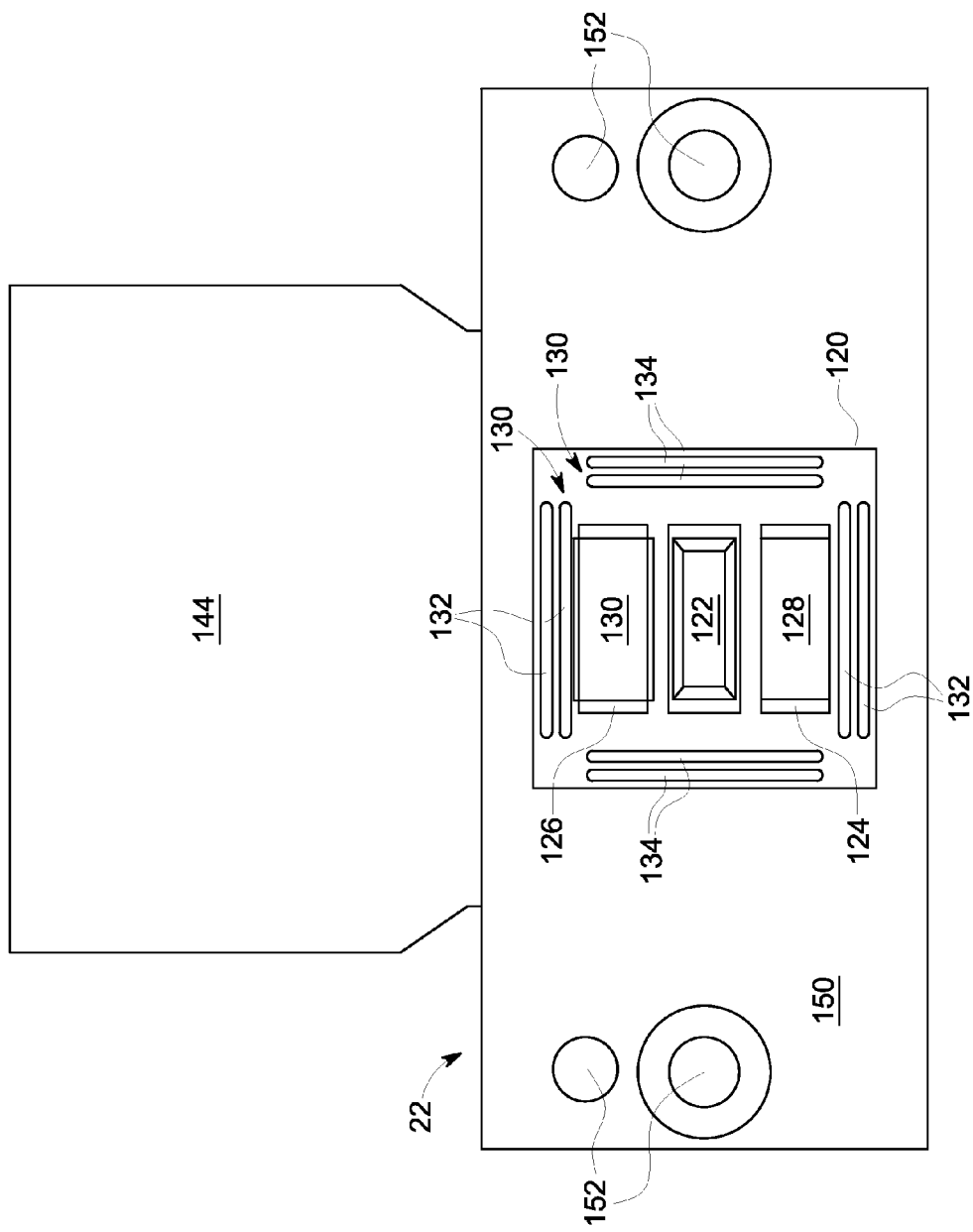
FIG. 5 depicts a plan view of a SSRD, in accordance with aspects of the present disclosure.

With this in mind, FIGS. 3-5 depict varying views of one example of an SSRD 22 suitable for use in accordance with the present disclosure. For example, FIG. 3 depicts an exploded view of an SSRD 22 while FIG. 4 depicts a perspective view of an assembled SSRD 22 and FIG. 5 depicts a plan view of the assembled SSRD 22. In the depicted example, the SSRD 22 includes an X-ray lens portion 120 that includes various apertures through which emitted X-rays may be filtered and/or directed onto the detection elements. For example, in the depicted example the X-ray lens 120 includes three central apertures through which X-rays may pass to impact the detection elements: an unfiltered reference normal aperture 122, a first filtered aperture 124, and a second filtered aperture 126. In the depicted example, the first and second filtered apertures 124 and 126 are each differently filtered (such as by first KvP filter 128 and second KvP filter 130) to provide different spectral information with respect to the emitted X-rays. In this manner, overall X-ray emissions may be determined via the reference normal aperture 122 while X-ray emission at different wavelengths of interest may be determined at via the respective filtered apertures 124 and 126. While the depicted example includes central apertures 124, 126, and 128 (which, as noted, may be useful for flux normalization and/or kVp measurement), it should be understood that the depicted central apertures are not required for determination of focal spot characteristics (e.g., size, shape, or location) as discussed herein. Therefore, in other embodiments, the central apertures 124, 126, 128 may be absent or provided elsewhere, such as in a second SSRD.

Turning back to the figures, in the depicted example, slits 130 are provided to the sides of the respective apertures 122, 124, 126. The slits 130 allow X-rays to pass through in a limited manner determined by the aspect ratio of the slits 130. In certain implementations, the aspect ratio of the slits is greater than or equal to 20 and/or less than or equal to 100. This limited transmission may be detected by the detection elements to yield the localized intensity measurement data 90, discussed herein, used to determine focal spot characteristics. In FIGS. 3 and 4, a single slit 130 is depicted in each side of the apertures 122, 124, and 126. In FIG. 5, a pair of slits 130 is depicted at each side of the apertures. In this example, therefore, the slits 130 are of two types, those having a first orientation (e.g., slits 132) and those having a second orientation orthogonal to the first (e.g., slits 134). The differently oriented slits 132 and 134 may be useful in providing localized intensity measurements 90 that provide information in two dimensions (e.g., x and y), which in turn may be useful in determining focal spot characteristics such as focal spot size 94 and focal spot shape 100 in each of those two dimensions. As will be appreciated, additional slits 130 may be provided in other embodiments relative to the four and eight slits depicted. Further, in other implementations other types of openings, such as holes, may be provided instead of slits 130 while still providing comparable localized intensity measurement data 90.

In the depicted example, the X-ray lens 120 may be mounted on or formed contiguously with a mounting substrate 150 having alignment and mounting features 152 that may be useful for mounting the assembly onto an external support, such as a portion of the collimator 14. The substrate 150 may have a corresponding aperture beneath where the X-ray lens 120 is mounted to allow X-rays passed by the X-ray lens 120 to reach detection elements, discussed below. In the depicted example, a blocker 154 (such as a 0.6 mm layer of tungsten) may also be provided to reduce the high X-ray flux present close to the X-ray source to the lower levels typically encountered by CT X-ray detectors. This reduction to the X-ray flux may allow the use of a standard CT detector assembly as the detecting element of the SSRD.

The respective apertures and slits of the X-ray lens 120 of the SSRD 22 (and the corresponding aperture of the substrate 150) allow some portion of the emitted X-rays to pass through the X-ray lens 120 and to reach detection elements positioned to receive the transmitted X-rays and to generate electrical signals in response to the transmitted X-rays. For example, in the depicted example, a layer 140 of scintillators is provided that convert incident X-rays to optical light photons. The optical light photons may then be detected by an array 142 of photodiodes (or other electronic light detecting elements) that may be readout by electrical circuitry and the acquired signal data communicated to downstream electrical components, such as via a suitably configured flex circuit 144 or other conductive path in communication with the data acquisition system 30.

Figure 6:
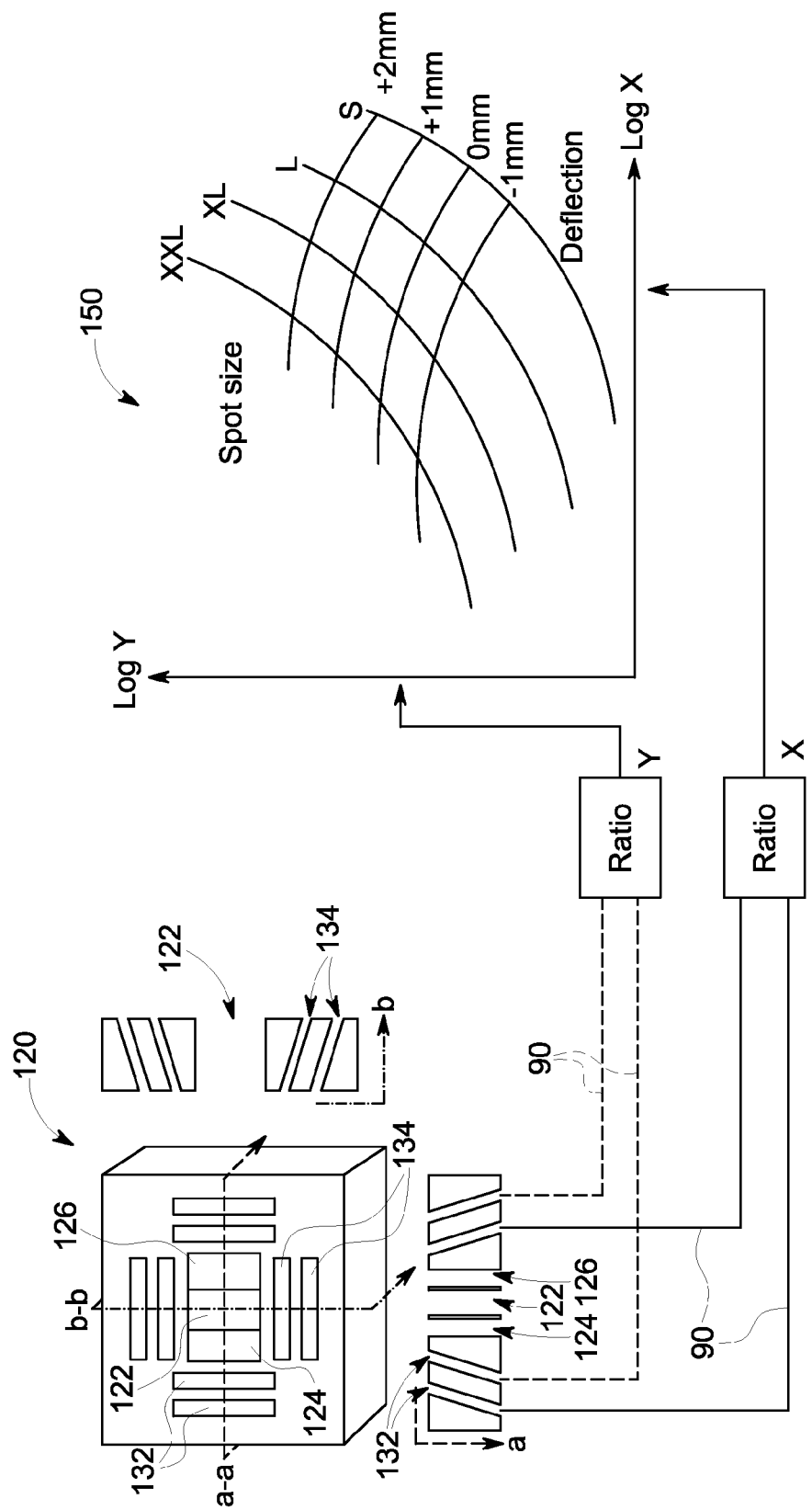
FIG. 6 depicts a combination perspective and cross-sectional view of an X-ray lens assembly and one use of such an X-ray lens assembly, in accordance with aspects of the present disclosure.

With this example of an SSRD 22 in mind, FIG. 6 depicts a schematic view of an X-ray lens 120 of a source-side reference detector 22. In the depicted example, the X-ray lens 120 is shown from a top perspective and includes various central apertures, including reference normal aperture 122. As noted above, in other embodiments, the central apertures may be absent. In addition, a pair of slits 130 are provided on each side of the apertures, including, in the depicted example, four slits 132 that are orthogonal to the depicted a-a plane and four slits 134 that are orthogonal to the depicted b-b plane. In the depicted example, the respective slits 130 are used to measure focal spot properties in orthogonal directions, such as in the x and y dimensions, though the slits themselves may not mathematically be orthogonal to one another due to the respective angular paths they take through the lens assembly. For example, cross-sectional views taken along sight lines a-a and b-b are depicted beside the top perspective view of the X-ray lens 120 which show the respective paths taken by the apertures and the by the slits 132 and 134 through the X-ray lens 120. In the depicted example, the apertures are straight passages through the X-ray lens 120 while the respective slits are angled relative to the apertures.

As discussed herein, X-rays passing through the angled slits provide localized intensity measurements 90 of X-ray incidence. In certain embodiments, the differential transmission of X-rays through slits of a given orientation (e.g., the x-orientation or the y-orientation in the depicted example) can provide useful information about the focal spot on the target associated with the emitted X-rays, such as the focal spot size or the focal spot location. By way of example, in FIG. 6 localized intensity measurements 90 corresponding to X-ray transmission through slits 132 may be used to derive ratios that may in turn be used to derive focal spot size and focal spot location (e.g., deflection) based on known relationships between focal spot location and size (as depicted in graph 150).

Figure 7:
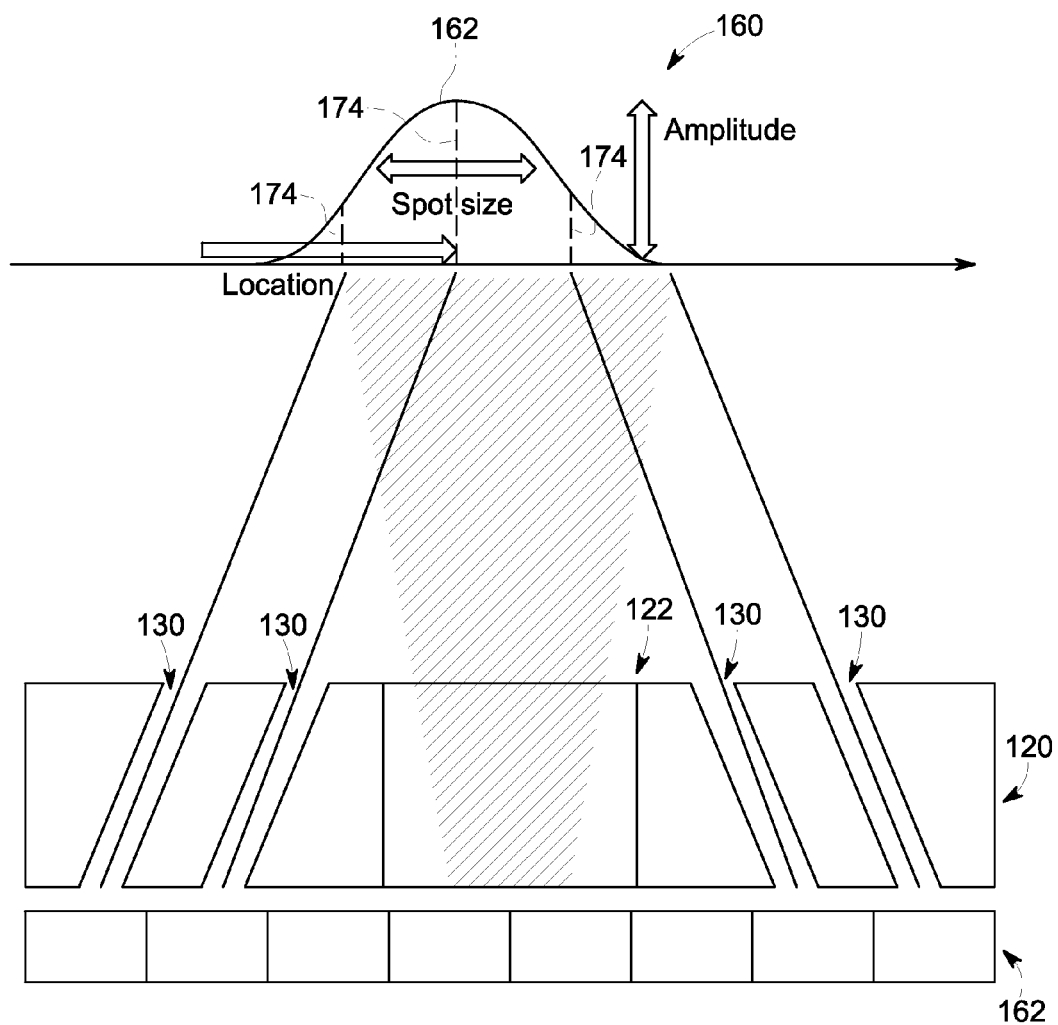
FIG. 7 depicts a cross-sectional view of an X-ray lens assembly describing the views through the various apertures of the assembly with respect to an X-ray emission site, in accordance with aspects of the present disclosure.

Turning to FIG. 7, this concept is further developed by reference to a cross section through X-ray lens 120 depicting slits 130 and reference normal aperture 122. In the depicted example, X-rays passing through the slits 130 and the reference aperture 122 impact pixilated detector elements 162 (which may include scintillator and photodiode elements as discussed above). The X-rays are emitted from a localized focal spot 160 on a target structure. In the depicted example, the focal spot 160 is represented as an intensity distribution 162 of emitted X-rays with respect to a line, wherein the distribution 162 reflects the location, amplitude, and size of the focal spot with respect to the line. As depicted in this example, non-localized X-ray emissions are detected though the reference normal aperture 122. Such non-localized X-ray emission data may be useful for determining the overall amplitude of the curve 162 (i.e., of the focal spot 160 at the represented plane), assuming the peak of the curve 162 is visible within the aperture 122.

Conversely, slits 130 due to their limited aperture and angled orientation, see only a portion of the curve 162 or, in some instance, none of the curve 162, as denoted by lines 174. Thus, measurements obtained at the detector elements 162 due to X-ray transmission through slits 130 constitute localized intensity measurements 90 corresponding to only a limited portion of the focal spot 160. Analysis and/or comparison of these separate localized intensity measurements 90 (such as by determining the ratios of certain localized measurements may be useful in determining the location and size of the focal spot 160 (and potentially the amplitude) on the target relative to a desired size and location. In general, three measurements (e.g., a measurement through reference normal aperture 122 and two of the slits 130) are needed to determine amplitude, size, and location of the focal spot 160. Thus, for each view, at least three slits 130 or at least two slits 130 and the reference normal aperture 122 should transmit X-rays emitted by the focal spot 160, even for deflected positions. As will be appreciated, additional slits 130 provide redundancy and may improve the robustness of the measurements acquired for non-Gaussian focal spot profiles.

Figure 8:
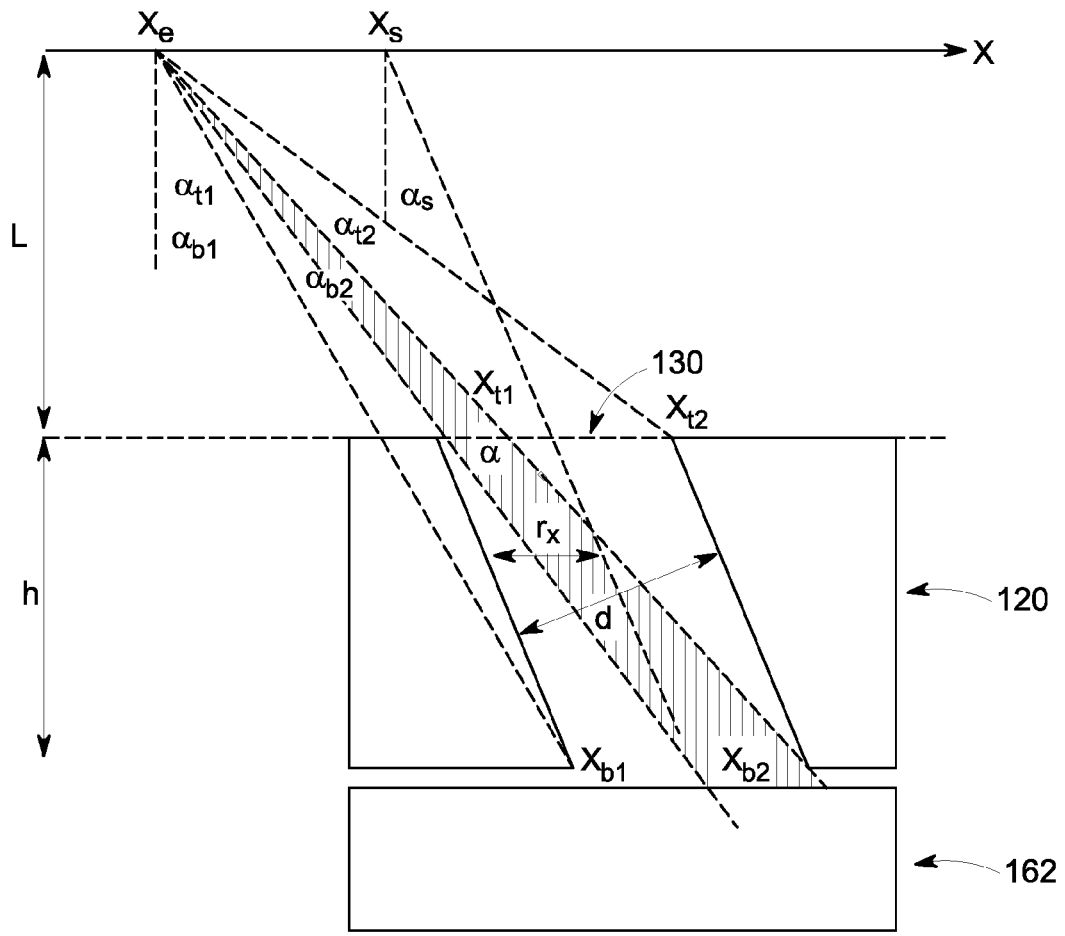
FIG. 8 depicts a cross-sectional view of a slit through an X-ray lens assembly along with descriptive parameters of the slit and assembly, in accordance with aspects of the present disclosure.

Turning to FIG. 8, an example of a one-dimensional calculation related to X-ray transmission through a slit 130 is provided. In this example, a cross section of a slit 130 is depicted along with a detector element 162 (e.g., a pixel of a detector). Various other elements related to the one-dimensional transmission calculation are also depicted, including: an emitting point, $x_e$, of the focal spot from which an X-ray is emitted; dimensions $x_s$, $\alpha_s$, and d of slit 130; height, h, of the X-ray lens 120, and distance, L, between the focal spot and the X-ray lens 120. In addition, FIG. 8 depicts the x-coordinates of the edges of the slit 130 as xt1, xt2, xb1, and xb2 (i.e., a pair of top and a pair of bottom x coordinates). The detector element 162 is illuminated between $\max(\alpha_{t1}, \alpha_{b1})$ and $\min(\alpha_{t2}, \alpha_{b2})$. Assumptions made for the present calculation include that the detector element 162 collects all of the light passing through the slit 130 and that one-dimensional analysis is appropriate, such as in the case of an infinitely large slit.

In accordance with the depicted elements:

$$r_x = \frac{d}{2\cos\alpha_s} \quad (1)$$

$$\alpha = \min(\alpha_{t2}, \alpha_{b2}) - \max(\alpha_{t1}, \alpha_{b1}) \quad (2)$$

$$\begin{aligned} x_{t1} &= x_s + L\sin\alpha_s - r_x \\ x_{t2} &= x_s + L\sin\alpha_s + r_x \\ x_{b1} &= x_s + (L+h)\sin\alpha_s - r_x \\ x_{b2} &= x_s + (L+h)\sin\alpha_s + r_x \end{aligned} \quad (3)$$

$$\begin{aligned} \alpha_{t1} &= \tan\frac{x_{t1} - x_e}{L} \\ \alpha_{t2} &= \tan\frac{x_{t2} - x_e}{L} \\ \alpha_{b1} &= \tan\frac{x_{b1} - x_e}{L+h} \\ \alpha_{b2} &= \tan\frac{x_{b2} - x_e}{L+h} \end{aligned} \quad (4)$$

The aspect ratio of the slit 130 is h/d. In practice, the lens height h may be limited by the available space where the SSRD 22 is installed. For example, in certain implementations, potential mechanical interference with the moving blades of the collimator 14 may limit the height h of the lens assembly 120. The diameter d of the slit 130 may be limited by manufacturing capabilities. As a result of these various considerations, aspect ratios greater than 20 may require more complicated processing, such as using two parts instead of cutting a slit 130 into a single part.

With the foregoing in mind, the impact of aspect ratio on focal spot size determination is discussed. As will be appreciated, the slit aspect ratio can affect how difficult or easy it is to determine focal spot size, with lower slit aspect ratios generally leading to more difficulty in determining focal spot size and higher slit aspect ratios making it easier to determine focal spot size. Conversely, however, lower slit aspect ratios may be better for determining focal spot location than higher aspect ratios. In the present discussion, it should be appreciated that the absolute numeric value of the aspect ratio may, by itself, be insufficient to establish whether an aspect ratio should be considered high or low in a given context. In particular, a given aspect ratio should be considered in the context of the respective length between the X-ray lens, L, and the height, h, of the lens, i.e., L/h. With this in mind, the examples of a low aspect ratio of 20 and a high aspect ratio of 100 given below may be proper in the circumstance where L/h=10, however, for other values of L/h the aspect ratio providing the same results may be different. For example, a slit aspect ratio of 20 with L/h=10 would give same result as a slit aspect ratio of 40 with L/h=20.

Figure 9:
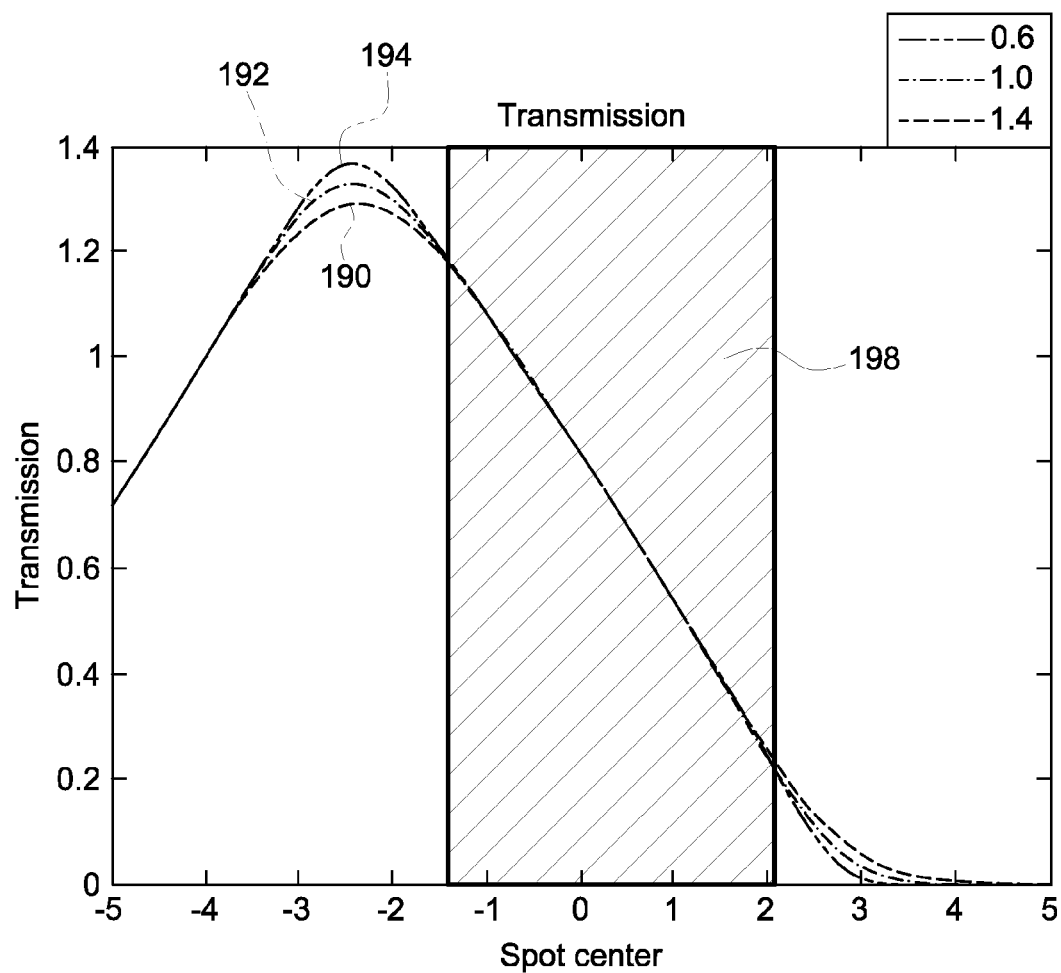
FIG. 9 depicts X-ray transmission as seen through a low aspect ratio slit, in accordance with aspects of the present disclosure.

For example, for a low slit aspect ratio (e.g., 20 with L/h=10), the penumbra region (i.e., the region on the target from which transmission to the detector pixel is between 100% and 0% of maximum transmission) associated with a respective slit 130 and associated detector element may be much larger than the focal spot size, and the observed measurements are more likely to fall within a region of linear decay of the transmission coefficient (which is indistinguishable for different spot sizes). If the focal spot is entirely within the penumbra region (which is more likely at low slit aspect ratios), the focal spot size has negligible effect on transmission integrated on the SSRD detector elements. Thus, focal spot size may not be determinable from the measured data at the SSRD due to the linearity of the signal as a function of spot location in the observed region. That is, the data associated with different spot sizes may only differ (and thus useful for distinguishing between different spot sizes) at a limited number of points (such as at the focal spot center and distribution tails), with other regions being co-linear at different focal spot locations, and thus unusable to differentiate different focal spot sizes. This is shown conceptually in FIG. 9, where curves 190, 192, and 194 are shown depicting transmission as a function of focal spot center for three different spot sizes as seen through a slit 130 having a low aspect ratio. As depicted, the low slit aspect ratio is associated with a single large measurement region 198 that may be insufficient to distinguish the curves associated with the different focal spot sizes. However, the low slit aspect ratio, which sees a large portion of the curves, may be well suited for determining a location of the focal spot.

Conversely, for a comparably high slit aspect ratio (e.g., 100 with L/h=10), the focal spot size may be much larger than the respective penumbra region associated with the slit 130 and associated detector element, and the focal spot size may have a large effect on transmission integrated at the respective SSRD detector element. Thus, at higher slit aspect ratio, the measured signal is strongly dependent on focal spot size. Thus, focal spot size may be more readily determinable from the measured data at the SSRD due to the transmission characteristics of focal spots of different sizes not being on the same line (i.e., not overlapping) over an extended range of focal spot locations. Therefore, for higher slit aspect ratios, it may be easier to determine focal spot size due to the measurements not overlapping (over a range of focal spot locations) to a great extent.

Figure 10:
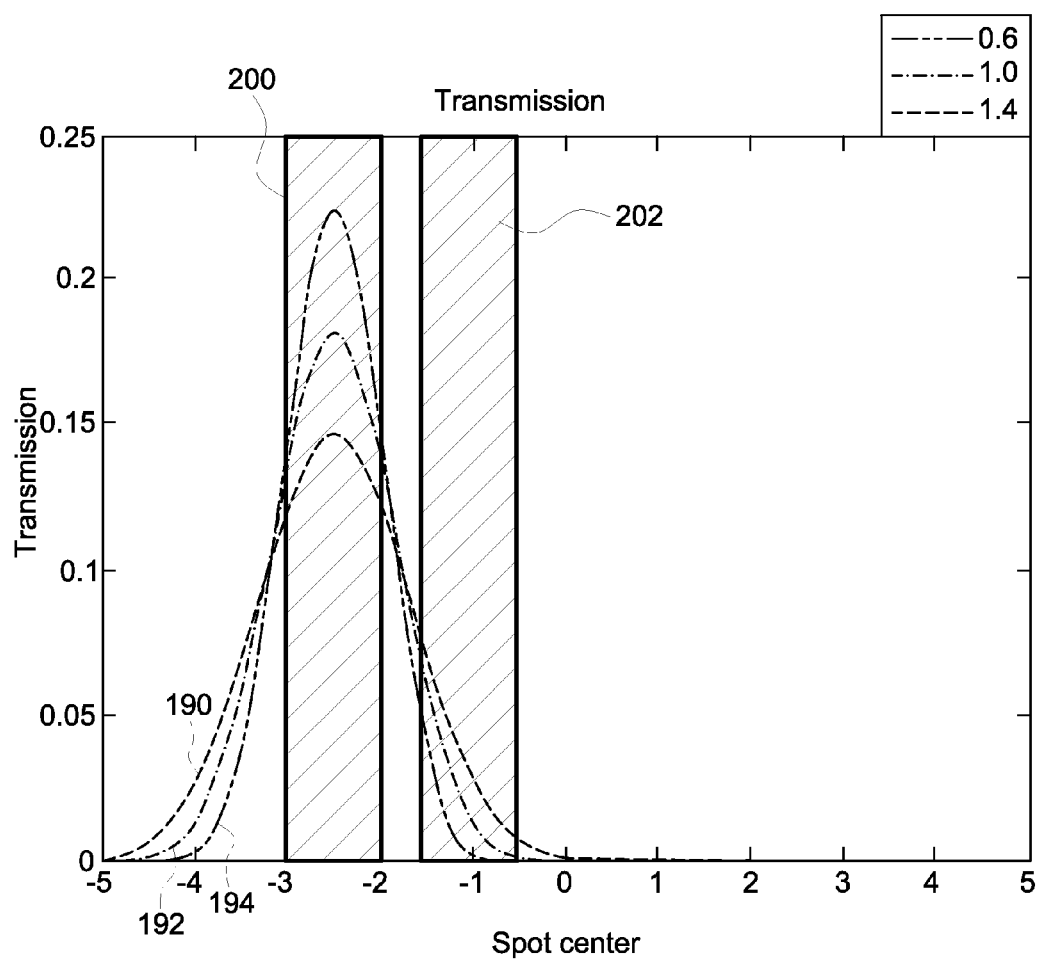
FIG. 10 depicts X-ray transmission as seen through a high aspect ratio slit, in accordance with aspects of the present disclosure.

This is shown conceptually in FIG. 10, where curves 190, 192, and 194 are shown depicting transmission as a function of focal spot center for three different spot sizes as seen through a slit 130 having a high aspect ratio. As depicted, the high slit aspect ratio is associated with a narrow measurement region 200 that may be suitable for distinguishing between the curves associated with the different focal spot sizes, i.e., the measured signal within the narrow measurement region 200 may be strongly dependent on focal spot size. However, as may also be noted, the high aspect ratio slit "sees" only a narrow region (e.g., measurement region 200) of the target and, therefore, may be poorly suited for determining focal spot location. With this in mind, it may be desirable to provide additional slits 130 (yielding additional measurement regions 202) to accurately measure focal spot size at each possible deflection location and to also provide sufficient information to allow accurate determination of focal spot location.

It may also be noted that, in one embodiment, for focal spot size measurement where there is only a single slit 130 (or a single hole, as discussed below) in each direction, the focal spot may be intentionally deflected onto different locations of the target. Transmission may then be measured as a function of spot deflection. As deflection is presumably known (and measurable by the SSRD 22), focal spot size can still be determined, even with fewer slits or holes, as discussed herein.

Figure 11:
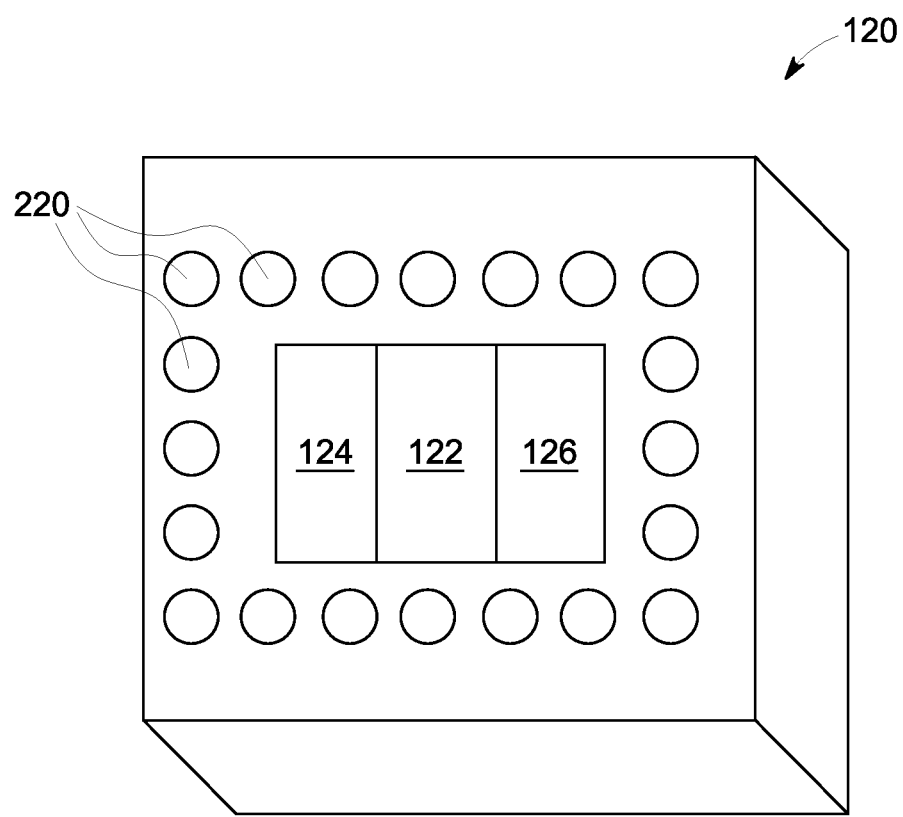
FIG. 11 depicts a perspective view of an X-ray lens assembly incorporating hole features, in accordance with aspects of the present disclosure.
Figure 12:
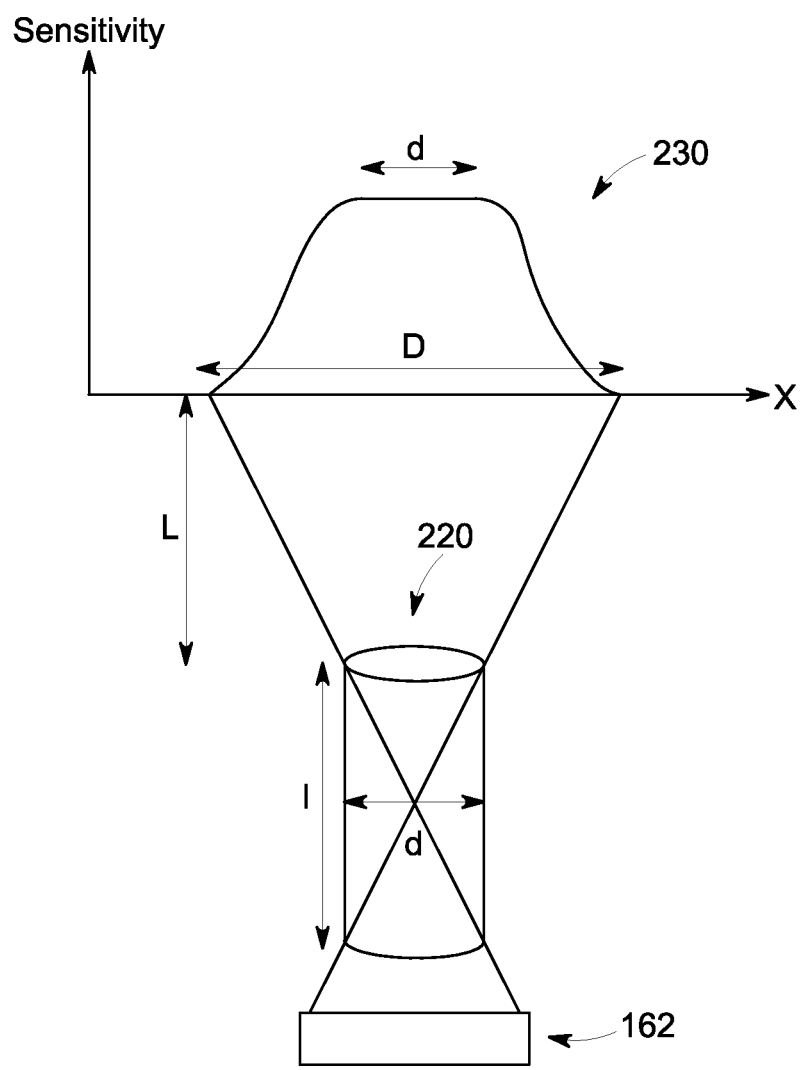
FIG. 12 depicts a schematic view of a hole through an X-ray lens assembly along with descriptive parameters of the hole and assembly, in accordance with aspects of the present disclosure.

While the preceding has described examples where localized intensity measurements are generated using slits 130, in other embodiments, other types of openings may be employed. For example, turning to FIGS. 11 and 12, an X-ray lens 120 having holes 220 instead of slits is depicted, where the bottom of each hole (i.e., the hole opening facing the detector elements) is aligned to a detector element (e.g., detector pixel). Though the embodiment of FIG. 11 depicts the holes 220 used in conjunction with the apertures 122, 124, 126, in other embodiments the apertures are not present and the holes 220 provide sufficient information to determine the focal spot characteristics of interest. In one implementation, each hole 220 is a long, thin hole having an aspect ratio determined as with slits 130. The holes 220 may be either tilted or angled with respect to the X-ray lens 120 body or may be vertical (i.e., straight through) the X-ray lens 120 such that the holes are perpendicular to the surface of the X-ray lens 120 facing the focal spot. As depicted in FIG. 12, an example of a hole 220 is depicted along with a corresponding sensitivity graph 230 depicting the maximum sensitivity (here shown along a single dimension, x) within a region that is the same size as the diameter d of hole 220. Each hole 220 integrates over a small region of the x-y deflection range. The outer bound of the integrated region is:

$$D=2*d*L/l \qquad (5)$$

For example, when d=0.05 mm, L=100 mm, and l=10 mm, then D=1 mm.

Figure 13:
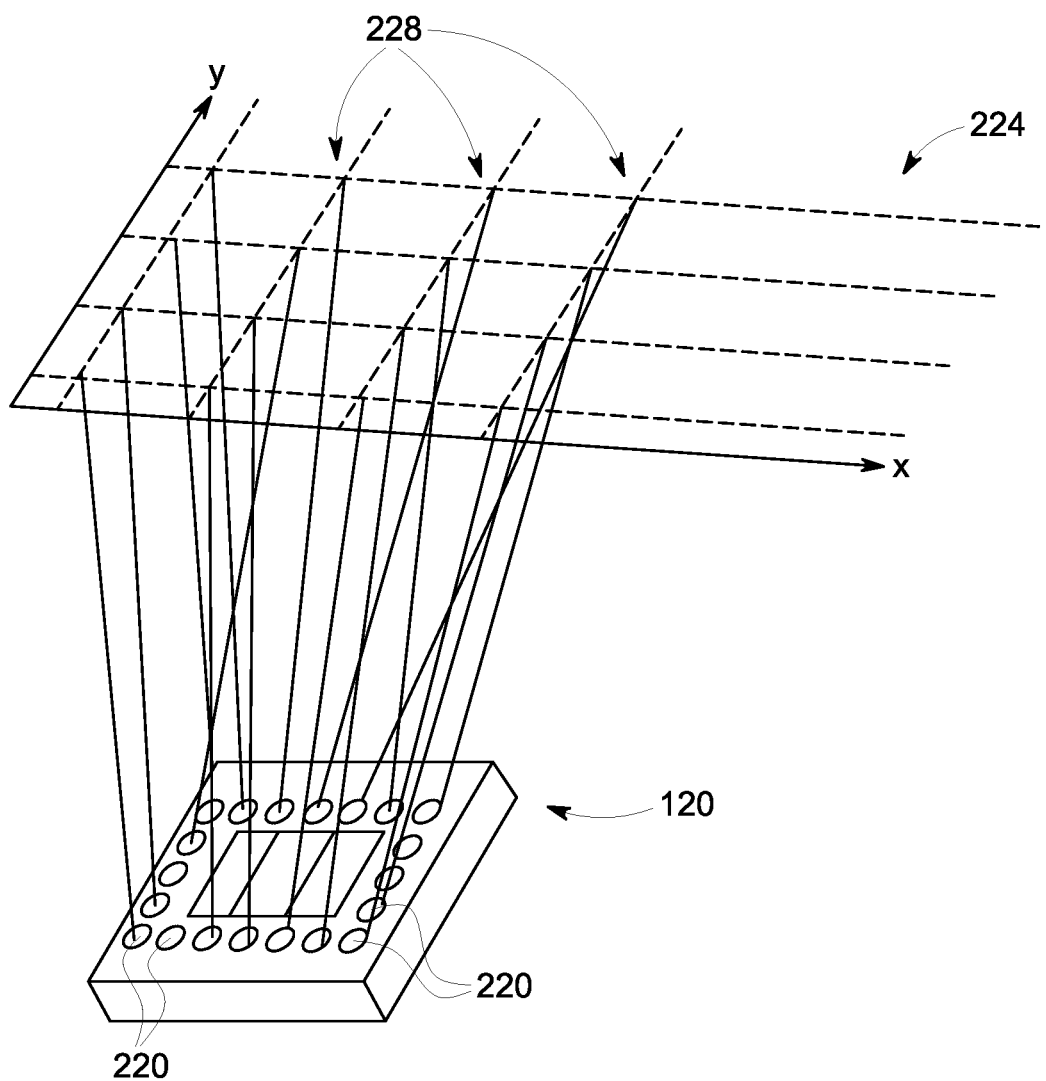
FIG. 13 depicts an X-ray lens assembly incorporating hole features and depicting sampling over an x-y deflection range, in accordance with aspects of the present disclosure.
Figure 14:
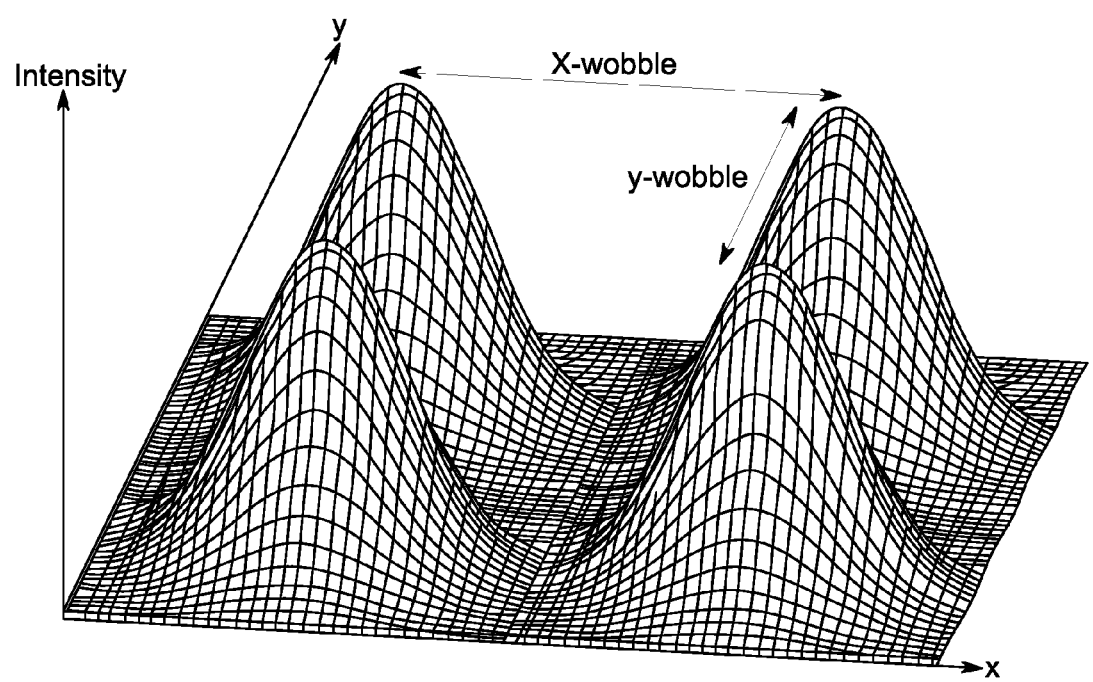
FIG. 14 depicts a graphical example of intensities observed at different x-y locations through the X-ray lens assembly of FIG. 13, in accordance with aspects of the present disclosure.

In one embodiment, depicted in FIGS. 13 and 14, each hole 220 is aligned to (i.e., points to) a different location 228 in the x-y deflection range 224. Instead of acquiring a line integral, the holes 220 allow acquisition of the intensity observed in small, circular regions. Thus, in embodiments employing holes 220, the corresponding detector elements 162 simultaneously measure x and y deflection over a large x-y range, such as the entire x-y deflection range.

Figure 15:
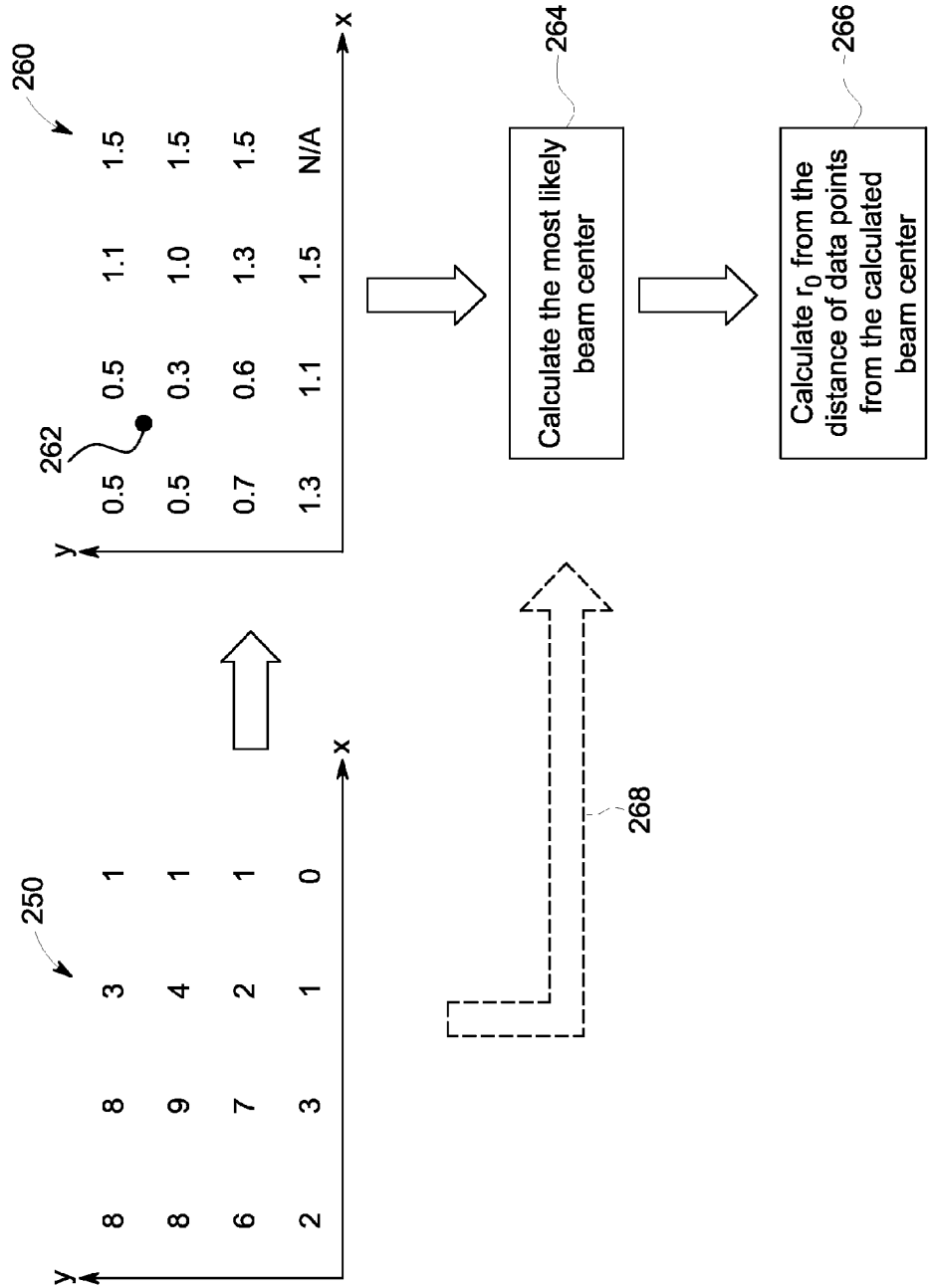
FIG. 15 depicts a flow diagram demonstrating determination of various characteristics of a focal spot, in accordance with aspects of the present disclosure.

Turning to FIG. 14, which depicts intensity measurements taken at such circular regions along an x-y deflection range, it can also be seen how such measurements can be used to determine or characterize the shape of a focal spot. That is, a collection of such intensities taken along the x-y grid can be used to characterize not only the center or location of the focal spot and the size of the focal spot, but also the general shape or outline of the focal spot. This can also be seen in FIG. 15, where a flow diagram incorporating x-y measurement data is depicted. Instead of the graphical three-dimensional distributions of FIG. 14, the example of FIG. 15 uses numerical measurements or values within the x-y range to facilitate explanation of certain aspects of the present approach. In this example, chart 250 (e.g., a 4×4 matrix) depicts measured beam intensity at different x-y locations measured by the holes 220 of an X-rays lens 120. In one example, Gaussian beam intensity can be characterized as:

$$I=I_0*\exp(-r^2/r_0^2) \qquad (6)$$

where r is the distance from the center of the focal spot. From the intensity measurements, the distance from the center of the focal spot center can be determined:

$$r/r_0=\sqrt{\ln(I_0/I)} \qquad (7)$$

where $I_0$ is the value measured or observed by the reference normal region of the detector (i.e., observed through reference normal aperture 122). This is depicted at chart 260, where measured beam center distance $r/r_0$ is shown for the corresponding x-y locations. In the depicted example, from this data, the most likely beam (i.e., focal spot) center 262 can be calculated (block 264) and the $r_0$ can be calculated (block 266) based on the distance of the data points from the calculated beam center. Alternatively, as depicted by dashed arrow 268, the beam center may instead be calculated directly from the beam intensity data of chart 250 (without going through the intermediary step of calculating the beam center distance values of chart 260), such as by calculating the center of gravity of the intensity distribution 250 or the center of gravity of a subset of the intensity distribution with the highest numbers. As will be appreciated, based on the calculated beam center 262, characteristics of the focal spot such as location and size may directly (or indirectly) derived. Likewise, based on the location and shape characteristics, characteristics of the focal spot shape may also be determined from the intensity data, for example, deviations from a circular Gaussian shape may be evident from unexpectedly high or low intensity values at the expected edges of the focal spot.

Technical effects of the invention include real-time characterization of focal spot characteristics in an X-ray generating system. Further technical effects include real-time control of an X-ray generating apparatus based upon one or more measured focal spot characteristics, such as size, location, and/or shape of a focal spot used to generate X-rays. Additional technical effects include controlling operation of a collimator and/or an image reconstruction process based on one or more measured focal spot characteristics.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A CT system, comprising:
an X-ray source, wherein the X-ray source is disposed on a first side of an imaging volume;
an imaging detector configured to generate a first set of electrical signals in response to a first portion of X-rays emitted by the X-ray source, wherein the imaging detector is disposed on a second side of the imaging volume opposite the first side;
a reference detector positioned on the first side of the imaging volume, wherein the reference detector is configured to generate a second set of electrical signals in response to a second portion of the X-rays emitted by the X-ray source, the reference detector comprising:
an X-ray assembly having three or more openings configured to transmit X-rays emitted from a focal spot, wherein at least two of the three or more openings are configured to transmit X-rays emitted at different localized sub-regions of the focal spot, and wherein a ratio of height to diameter of each of the at least two of the three or more openings is about 20 or greater;
a data acquisition system configured to receive the first set of electrical signals from the imaging detector and the second set of electrical signals from the reference detector; and
a processing component configured to process the second set of electrical signals to generate one or both of a size or a shape of a focal spot associated with X-ray emission by the X-ray source.

2. The CT system of claim 1, wherein the focal spot is the spot on a target material impacted by an electron beam.

3. The CT system of claim 1, comprising:
an X-ray controller configured to control operation of the X-ray source, wherein the X-ray controller is configured to adjust its operation based on one or both of the size or shape of the focal spot.

4. The CT system of claim 1, wherein the processing component is further configured to adjust reconstruction of an image from the first set of signals based on one or both of the size or shape of the focal spot.

5. The CT system of claim 1, comprising:
a collimator assembly positioned on the first side of the imaging volume, wherein the collimator is configured to limit the X-rays transmitted from the X-ray source to the imaging detector and wherein the reference detector is positioned on the collimator assembly.

6. The CT system of claim 5, wherein the collimator is adjusted based on one or both of the size or shape of the focal spot.

7. The CT system of claim 1, wherein the reference detector comprises at least:
an X-ray lens assembly comprising three or more openings configured to transmit X-rays emitted from the focal spot, wherein at least two of the openings are configured to transmit X-rays emitted at respective localized sub-regions of the focal spot.

8. The CT system of claim 7, wherein the three or more openings comprise:
at least one central aperture configured to transmit X-rays emitted by the X-ray source; and
two or more slits or holes on opposing sides of the central aperture, wherein each slit or hole is configured to transmit X-rays for a localized sub-region of the focal spot.

9. A reference detector, comprising:
an X-ray lens assembly comprising three or more openings configured to transmit X-rays from a focal spot associated with emission of the X-rays, wherein at least two of the three or more openings are configured to transmit X-rays emitted at different localized sub-regions of the focal spot, and wherein a ratio of height to diameter of each of the at least two of the three or more openings is about 20 or greater; and
a detection array configured to generate electrical signals in response to the X-rays transmitted by the X-ray lens assembly.

10. The reference detector of claim 9, wherein the three or more openings comprise:
at least one central aperture, wherein the at least one central aperture is configured to transmit X-rays emitted by a majority or all of the focal spot; and
two or more slits, wherein each slit is configured to transmit X-rays for a localized sub-region of the focal spot.

11. The reference detector of claim 9, wherein the three or more openings comprise a plurality of holes, each hole configured to transmit X-rays for a localized sub-region of the focal spot.

12. The reference detector of claim 9, wherein the respective openings are configured to measure focal spot characteristics in orthogonal directions.

13. The reference detector of claim 9, wherein the three or more openings are angled relative to a surface of the X-ray lens assembly facing the focal spot.

14. The reference detector of claim 13, wherein an aperture and an angle associated with each opening determines the localized sub-region of the focal spot seen by each respective opening.

15. The reference detector of claim 9, wherein the detection array comprises:
an array of scintillator crystals positioned on one side of the X-ray lens assembly; and
an array of photodiodes positioned to generate the electrical signals when the scintillator crystals are impacted by the X-rays transmitted by the X-ray lens assembly.

16. The reference detector of claim 9, comprising:
a mounting substrate to which the X-ray lens assembly is affixed, the mounting substrate comprising two or more mounting holes configured to mount the reference detector to a collimator assembly.

17. A method for characterizing an X-ray generation focal spot, comprising:
during operation of an X-ray source, acquiring localized intensity measurements from a reference detector, the reference detector comprising an X-ray assembly having three or more openings configured to transmit X-rays emitted from a focal spot, wherein at least two of the three or more openings are configured to transmit X-rays emitted at different localized sub-regions of the focal spot, and wherein a ratio of height to diameter of each of the at least two of the three or more openings is about 20 or greater, and wherein the localized intensity measurements are associated with a focal spot of the X-ray source;

determining one or more characteristics of the focal spot; and providing the one or more characteristics of the focal spot to a processing component or controller to adjust operation or collimation of the X-ray source.

18. The method of claim 17, wherein the one or more characteristics of the focal spot comprise one or more of a size, a shape, or a location of the focal spot.

19. The method of claim 18, comprising:

acquiring a set of projection data from an imaging detector;

providing the one or more characteristics of the focal spot to the processing component; and using the processing component, reconstructing the set of projection data to generate a diagnostic image, wherein the reconstruction utilizes the one or more characteristics of the focal spot.

20. The method of claim 17, wherein the localized intensity measurements are generated based on X-ray transmission through two or more slits or holes on the reference detector.

* * * * *